United States Patent [19]

Matsumoto

[11] Patent Number: 5,076,274
[45] Date of Patent: Dec. 31, 1991

[54] NON-CONTACT TONOMETER

[75] Inventor: Kazuhiro Matsumoto, Kawasaki, Japan

[73] Assignee: Canon Kabushiki Kaisha, Tokyo, Japan

[21] Appl. No.: 577,076

[22] Filed: Sep. 4, 1990

Related U.S. Application Data

[63] Continuation of Ser. No. 474,670, Feb. 6, 1990, abandoned, which is a continuation of Ser. No. 153,788, Feb. 8, 1988, abandoned.

[30] Foreign Application Priority Data

Feb. 18, 1987 [JP] Japan ................................ 62-36203

[51] Int. Cl.$^5$ ................................................ A61B 3/16
[52] U.S. Cl. ................................ 128/645; 128/648; 128/652
[58] Field of Search .................... 128/645, 648, 652

[56] References Cited

U.S. PATENT DOCUMENTS

| | | | |
|---|---|---|---|
| 3,585,849 | 6/1971 | Grolman | 128/648 |
| 3,756,073 | 9/1973 | Lavallee et al. | 128/648 |
| 3,832,890 | 9/1974 | Grolman et al. | 128/648 |
| 3,882,718 | 5/1975 | Kriebel | 128/648 |
| 4,705,045 | 11/1987 | Nishimura | 128/648 |
| 4,724,843 | 2/1988 | Fisher | 128/648 |

FOREIGN PATENT DOCUMENTS 182621 6/1986 European Pat. Off. ............ 128/648

Primary Examiner—Lee S. Cohen
Assistant Examiner—J. P. Lacyk
Attorney, Agent, or Firm—Fitzpatrick, Cella, Harper & Scinto

[57] ABSTRACT

An eye pressure meter provided with a pressing system for deforming the cornea of an eye to be examined, a detecting system for detecting the speed of deformation of the cornea, and a calculating system for calculating eye pressure value information on the basis of the information of the speed of deformation.

30 Claims, 4 Drawing Sheets

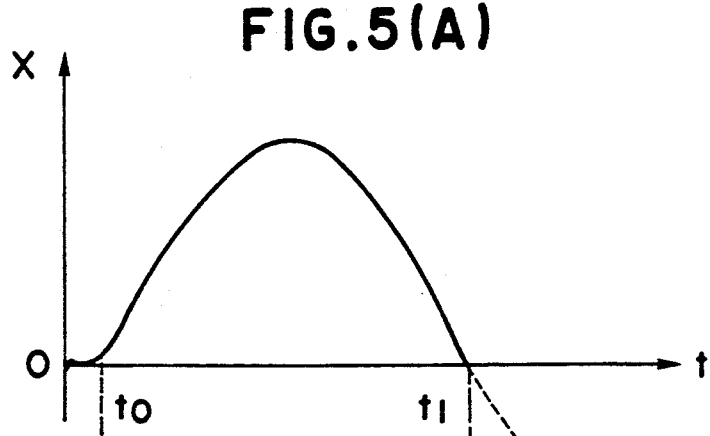
FIG.5(A)
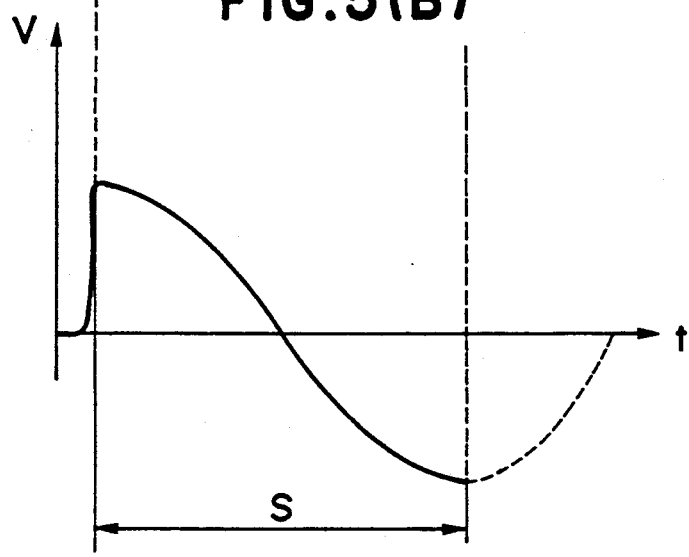
FIG.5(B)
FIG.5(C)
FIG.5(D)
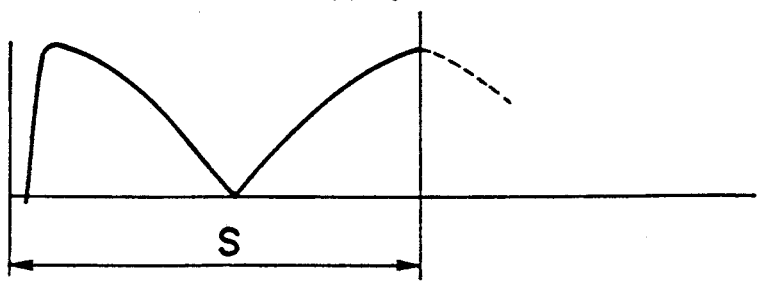

NON-CONTACT TONOMETER

This application is a continuation of application Ser. No. 474,670, filed Feb. 6, 1990, now abandoned, which is a continuation of application Ser. No. 153,788, filed Feb. 8, 1988, now abandoned.

BACKGROUND OF THE INVENTION

1. Field of the Invention

This invention relates to an eye pressure meter utilizing the deformation of a cornea which is for use in an ophthalmic hospital or the like.

2. Related Background Art

Heretofore, an apparatus of this type, as is known from U.S. Pat. No. 3,585,849, etc., has detected the quantity of reflected light from a cornea to thereby detect the predetermined deformation of the cornea, thus finding the eye pressure therefrom. Particularly, the apparatus shown in U.S. Pat. No. 3,585,849 is designed to project a light beam from outside the optic axis toward the cornea, detect the quantity of reflected light from the cornea by a photoelectric element disposed outside the optic axis and know a state in which the cornea is pressed flat.

However, in the prior art, the deformation of the cornea has been found by detecting the quantity of reflected light from the cornea and therefore, a measurement error has occurred when the quantity of light of the light source varies during measurement, and to prevent this, the stability of the light source has been required.

Also, measurement has been compelled to be done with the distance in the direction of the optic axis between an eye to be examined and the apparatus, i.e., the so-called working distance, being strictly adjusted.

SUMMARY OF THE INVENTION

It is an object of the present invention to provide a novel eye pressure meter in which the accuracy of measurement of eye pressure is not affected even if the quantity of light of a light source for detecting the deformation of a cornea fluctuates with time.

It is also an object of the present invention to provide an eye pressure meter which enables a wide tolerance of the working distance to be secured.

It is a further object of the present invention to provide an eye pressure meter which requires no examiner but enables the measurement of eye pressure to be accomplished by an examinee alone.

BRIEF DESCRIPTION OF THE DRAWINGS

FIGS. 3 and 5(A)-(D) show the variation in frequency when a cornea restores its original state with pulse air pressure applied thereto.

DESCRIPTION OF THE PREFERRED EMBODIMENT

Figure 1:
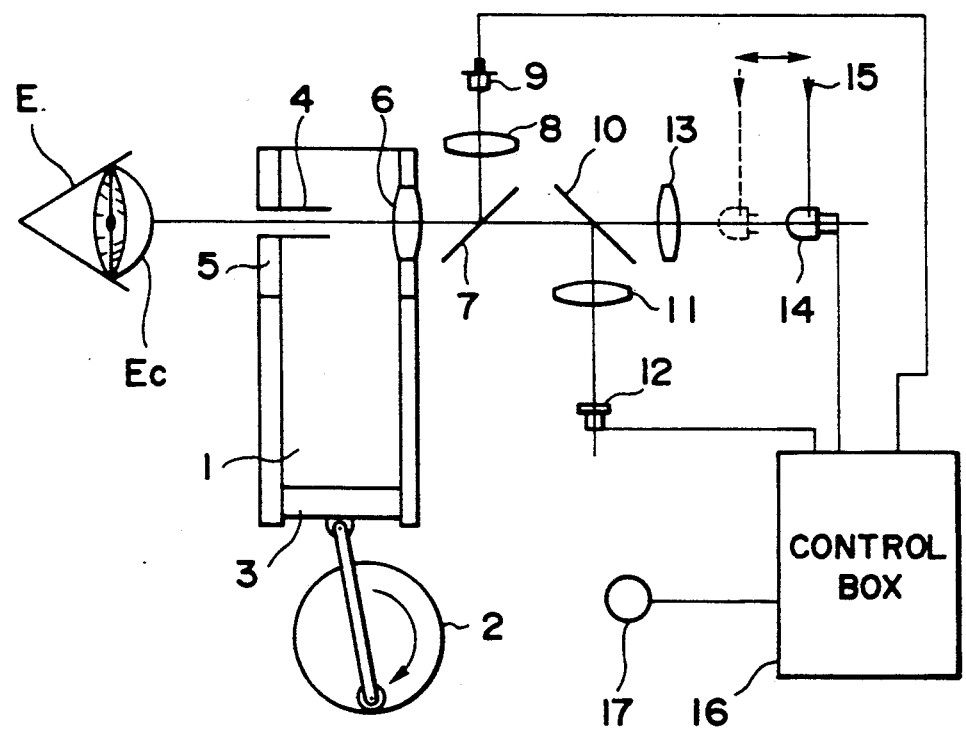
FIG. 1 shows an embodiment of the present invention.

FIG. 1 shows an embodiment of the present invention which is designed such that the air in a compressed air chamber 1 is driven by a solenoid 2, is compressed by a piston 3 and is blown from a nozzle 4 against the cornea Ec of an eye E to be examined. A planar member 5 is disposed in that portion of the compressed air chamber 1 which faces the eye E to be examined, and the nozzle 4 is attached to this planar member 5. An objective lens 6 is mounted on that surface of the compressed air chamber 1 which is opposed to the planar member 5. A half-mirror 7 is disposed rearwardly of the objective lens 6, and a lens 8 and a light source 9 are disposed in the direction of reflection of the half-mirror. A dichroic mirror 10 which reflects infrared light and transmits visible light therethrough is disposed in the direction of transmission of the half-mirror 7, and a lens 11 and a photoelectric converting element 12 are disposed on the optic axis in the direction of reflection of the half-mirror. A lens 13 and a light source 14 for fixation are disposed in the direction of transmission of the dichroic mirror 10, and the light source 14 for fixation is movable by a lever 15 in conformity with the examinee's visibility. The reference numeral 16 designates a control box having the calculating function, and the reference numeral 17 denotes a measuring switch.

Figure 2:
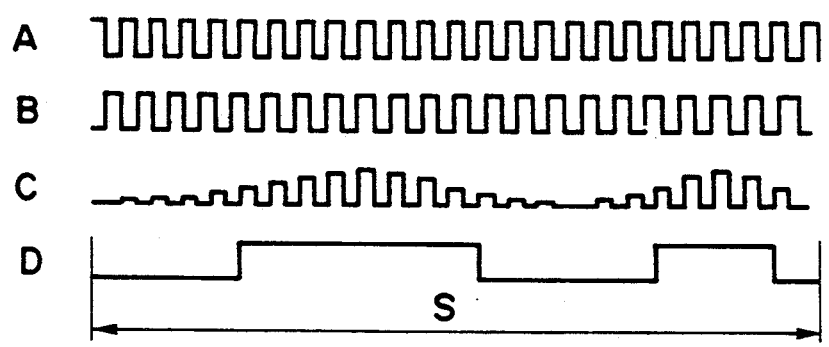
FIG. 2 is a waveform graph showing basic signals for measurement.

Looking into the nozzle 4 while keeping a predetermined distance from the objective lens 6, the examinee sees the flicker of the light source 14 for fixation. When it is difficult to see the flicker clearly, the examinee can use the lever 15 to adjust the light source 14 for fixation to a position in which it can be readily seen. The light source 9 is an infrared light source such as an infrared LED or a semiconductor laser provided substantially on the optic axis of the objective lens 6, and is turned on by a high frequency pulse, and a thin light beam therefrom passes through the lens 8, is reflected by the half-mirror 7 and is projected onto the cornea EC through the objective lens 6 and the nozzle 4. The reflected light from the cornea EC passes through the nozzle 4 and the objective lens 6 again, is transmitted through the half-mirror 7, is reflected by the dichroic mirror 10 and is directed through the lens 11 to the photoelectric converting element 12 provided substantially on the optic axis of the objective lens 6. When the photoelectric converting element 12 detects the reflected light of the light source 9 from the cornea EC, it is judged that the aligned state in a direction perpendicular to the optic axis is good, and the light source 14 for fixation stops flickering by the control box 16 and remains turned on, and the examinee knows that the alignment in the direction perpendicular to the optic axis has been completed. If the light source 9 and the photoelectric converting element 12 are made substantially conjugate with the cornea (conjugate, for example, with the cornea before deformed), the quantity of light received by the photoelectric converting element 12 can be presupposed and the alignment in the direction of the optic axis is also possible from the judgment as to whether the quantity of light received reaches the presupposed value. When after the completion of the alignment, the examinee depresses the measuring switch 17, the solenoid 2 is driven and the air compressed by the piston 3 is blown against the cornea Ec of the eye to be examined through the nozzle 4. The cornea Ec is deformed by the air pressure. A feature of the present apparatus is that the speed of deformation of the cornea is found with the aid, for example, of the Doppler effect of a high frequency pulse and the value of the eye pressure is found on the basis of said speed of deformation. The fundamental principle thereof is shown in FIG. 2. A is an output signal of a basic pulse for causing the light source 9 to emit a light. B is the output signal of the photoelectric converting element 12. Since the cornea is displaced toward the eye fundus by the air pressure, the frequency is lower than A due to the Doppler effect. That is, when the frequency of the pulse light impinging on the cornea is F and the frequency of the pulse light reflected from the cornea is F' and the speed of deformation of the cornea is V and the velocity of the light is C, $F - F'/F = V/C$.

If the output signals A and B are added together, the output signal thereof assumes a waveform as shown by C, and when waveform shaping is effected except for the high frequency component thereof, there appears a frequency signal corresponding to the difference between A and B, as shown at D. It is clear from the above-mentioned equation that the speed of deformation V of the cornea can be found from this frequency displacement $F - F'$.

It is known that the pressure value is varied with time so as to assume a predetermined pressure distribution and the air pressure is made to act on the cornea and the eye pressure of the eye to be examined can be found from the time when predetermined cornea deformation is reached.

Accordingly, said speed of deformation V of the cornea is integrated by time to find the amount of deformation and the eye pressure of the eye to be examined can be calculated from the time T when a predetermined amount of deformation $X_0$ is reached. More specifically, the predetermined amount of deformation $X_0$ is $X_0 = \int^T_0 V dt$, and as means for confirming that the cornea has been deformed by the predetermined amount of deformation $X_0$, use is made of the cornea shape measuring apparatus as known, for example, from Japanese Laid-Open Patent Application No. 50937/1983.

Figure 4A:
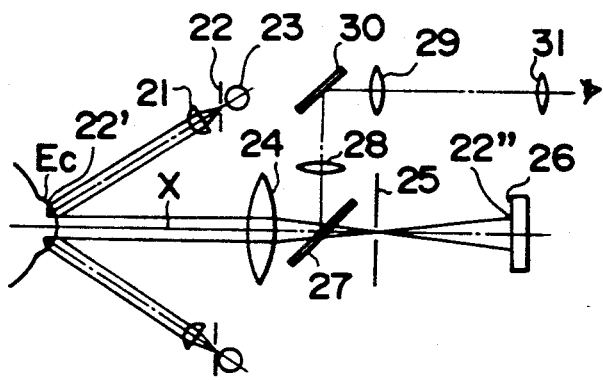
FIGS. 4 (A), 4(B) and 4(C) illustrate the manner in which a predetermined amount of deformation of the cornea is calculated from a variation in the radius of curvature of the cornea.
Figure 4B:
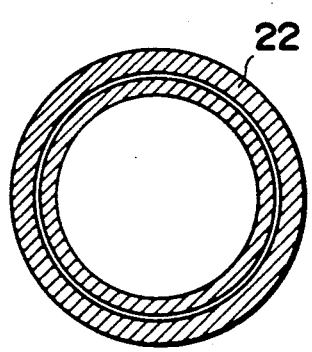

That is, as shown in FIGS. 4(A) and 4(B), a ring-like index mark 22 illuminated by a light source 23 is projected onto the cornea Ec from infinity in each meridian direction through a ring-like cylindrical lens 21 and a corneal reflection image 22' (a virtual image) is formed by the convex mirror action of the cornea Ec. The corneal reflection image 22' is formed as a corneal reflection image 2" on a position detecting element 26 through an objective lens 24 and a stop 25 disposed near the rearward focus position of the objective lens 24, and the radius of curvature of the cornea is calculated from the shape, particularly, the radius of the corneal reflection image 22".

The alignment of the cornea Ec and the measuring system is accomplished through a light dividing mirror 27, a relay lens 28, a mirror 30, a relay lens 29 and an eyepiece 31.

Figure 4C:
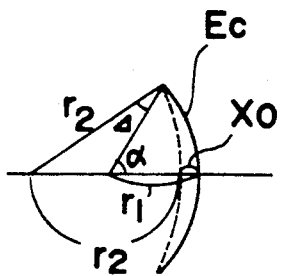

Assuming here that as shown in FIG. 4(C), the cornea has changed from a radius of curvature $r_1$, to a radius of curvature $r_2$, the following equation is established:

$$r_2/\sin\alpha = (r_2 + X_0 - r_1)/\sin\Delta = r_1/\sin(\alpha - \Delta),$$

where $\alpha$ and $\Delta$ are the angles shown in FIG. 4(C). If $\Delta$ is small, approximation will result in:

$$X_0 = (r_2 - r_1) \times (1/\cos\alpha - 1).$$

An embodiment using a pressing system in which the pressure is variable with time has been shown above, but besides it, it has been proposed that as a pressing system, use is made of a system which applies a predetermined air pressure to the cornea in a pulse-like fashion and the eye pressure of the eye to be examined is found from the amount of deformation of the cornea.

Accordingly, said speed of deformation V of the cornea is integrated by time to find the amount of deformation, and the eye pressure of the eye to be examined can be calculated from the amount of deformation X when said speed of deformation V has been time-integrated for a predetermined time. More specifically, the amount of deformation X is $\int_{T_{00}} V dt$ (where $T_0$ is the time when the deformation of the cornea is considered to be stable).

Further, besides what has been described above, the eye pressure of the eye to be examined may be calculated from the time when the speed of deformation V of the cornea assumes an extremal value.

Figure 3:
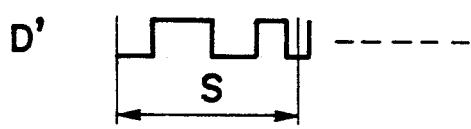

That is, if an air pulse is applied to the cornea, the cornea is generally deformed and restores its initial state in a time S with the aid of the eye pressure. Along therewith, the waveform shown in FIG. 2D depicts a waveform as shown by D' in FIG. 3 in which the frequency varies in conformity with the variation in the speed of deformation. The time interval between the two peaks of the waveform obtained by demodulating the waveform D' corresponds to the eye pressure. That is, if the eye pressure is high, the time interval becomes short, and if the eye pressure is low, the time interval becomes long. This will be described in detail below with reference to FIGS. 5(A)-(D).

FIG. 5(A) shows the manner of deformation. In this Figure, the ordinate X represents the distance of displacement of the cornea on the optic axis, and the abscissa t represents time. FIG. 5(B) shows the manner of variation in the speed of deformation. FIG. 5(C) graphically shows the waveform corresponding to the waveform D of FIG. 2. FIG. 5(D) shows a waveform obtained by demodulating the waveform of FIG. 5(C). At a time to immediately after the cornea has begun to be deformed, the speed of deformation of the cornea assumes a maximum value. The speed of deformation gradually becomes slower due to the eye pressure, and soon stops and begins to move in the opposite direction to restore its original shape. The speed gradually becomes faster and assumes a maximum value at a time $t_1$ when the vicinity of the original position has been reached. Generally, the period of vibration is in inverse proportion to the square root of the internal pressure and therefore, the eye pressure can be found from S.

Further, it is also possible to calculate the eye pressure of the eye to be examined directly from the speed of deformation of the cornea. More specifically, when for example, the correlation between the speed of deformation of the cornea in the initial pressed state and the eye pressure of the eye to be examined is known in advance, the eye pressure of the eye to be examined can be calculated directly from the speed of deformation of the cornea in the initial pressed state.

Now, in the present invention, the speed of deformation of the cornea is found as the cornea deformation detecting system and therefore, no high accuracy is required for the adjustment of the working distance between the cornea deformation detecting system and the eye to be examined. When the pressing system for deforming the cornea is incorporated into the apparatus body with the cornea deformation detecting system and the two systems are moved as a unit in the direction of the optic axis, the cornea deformation detecting system still detects the deformation of the cornea correctly, but the pressing system for deforming the cornea does not cause a predetermined pressure to act on the cornea because the distance in the direction of the optic axis to the eye to be examined varies and the pressure acting on the cornea varies, and thus accurate measurement of the eye pressure cannot be accomplished. So, the amount of variation in the distance in the direction of the optic axis from the nozzle 4 to the eye to be examined is corrected by any correcting means. Generally, the measured value of the eye pressure is also varied by a variation in the atmospheric pressure and therefore, it is desirable to correct also the amount of variation corresponding to the variation in the atmospheric pressure.

Now, in the embodiment described above, the light source has been caused to emit pulse light, but alternatively, a shutter (such as a mechanical shutter or a liquid crystal shutter) may be provided in the optical path so that pulse light may be extracted by the shutter. Also, in the previously described embodiment, the cornea has been deformed by an air stream, but alternatively, an ultrasonic wave may be used. In such case, the ultrasonic wave may preferably be converged on the cornea. Further, in the previously described embodiment, the variation in frequency has been detected by the utilization of the Doppler effect to find the speed of deformation of the cornea, but alternatively, the variation in wavelength may be detected as is apparent.

That is, when the wavelength of the light impinging on the cornea is $\lambda$ and the wavelength of the light reflected from the cornea is $\lambda'$ and the speed of deformation of the cornea is V and the velocity of the light is C, $\lambda(1/\lambda - 1/\lambda') = V/C$. In this case, the light impinging on the cornea need not be pulse light, but may be continuous light. Apparently, infrared light is preferable. Further, in this case, the photoelectric converting element 12 can be replaced by a spectrophotometer.

Also, the aforedescribed embodiment has been shown as an apparatus by which the examinee measures by himself or herself, but observation means may be provided to thereby construct a non-contact eye pressure meter which requires an examiner.

Further, in the aforedescribed embodiment, the fixation target has been a light source, but alternatively, a so-called starburst and a chart like scenery may be used.

Also, the fixation target has been made movable, but alternatively, the lens system may be made movable to adjust the visibility.

Also, the light emitting state before the alignment of the fixation target may be the turned-on state and the light emitting state after the alignment of the fixation target may be the flickering state.

What is claimed:

1. A non-contact tonometer comprising:
a pressurizing system, a deformation detection system, and a calculation system, wherein:
said pressurizing system includes:
fluid pressurizing chamber means for providing pressurized fluid; and
nozzle means for applying the pressurized fluid to deform a cornea of an eye to be examined, said nozzle means being coupled to said fluid pressurizing chamber means and adapted to be positioned opposite to the eye along a pressurization axis;
said deformation detection system includes:
light projection means for projecting a pulsed light beam to the cornea,
light receiving means for receiving a light beam reflected by the cornea during the deformation of the cornea; and
deformation speed detecting means for detecting the moving speed of the corneal surface being deformed in the direction of the pressurization axis on the basis of a frequency deviation between pulsed light beam projected to the cornea and the pulsed light beam reflected by the cornea;
said calculation system includes:
calculation means for calculating the eye pressure in accordance with the time integration of an output from said deformation speed detecting means.

2. A non-contact tonometer according to claim 1, wherein said light projection means and said light receiving means are coaxially arranged with said nozzle means.

3. A non-contact tonometer according to claim 1, wherein said calculation means includes means which calculates the eye pressure on the basis of a time period until the time integrated value of the output of said deformation speed detecting means reaches a predetermined value.

4. A non-contact tonometer according to claim 1, wherein said calculation means includes means which calculates the eye pressure on the basis of the time integrated value of the output of said deformation speed detecting means at a time after a predetermined time interval has expired.

5. A non-contact tonometer according to claim 1, wherein said fluid pressurizing chamber means includes means for providing pressurized air to said nozzle means.

6. A non-contact tonometer according to claim 1, wherein said fluid pressurizing chamber means includes means for varying the pressure of the fluid output from said nozzle means over time.

7. A non-contact tonometer according to claim 1, wherein said fluid pressurizing chamber means includes means for providing the fluid output from said nozzle means in a pulse state and at a constant pressure.

8. A non-contact tonometer according to claim 1, wherein said light projecting means includes means for projecting infrared light.

9. A non-contact tonometer according to claim 1, wherein a light source in the light projection means and a light receiving element in the light receiving means are optically conjugately arranged with the corneal surface the eye and the corneal surface is appropriately aligned with said light source and said light receiving element before measurement of the eye pressure.

10. A non-contact tonometer according to claim 9, further comprising an indicating means for indicating that the alignment of the eye is appropriate when the output of said light receiving element reaches a predetermined value.

11. A non-contact tonometer according to claim 1, further comprising a fixation means for fixing a gazing point of the eye along the pressurization axis.

12. A non-contact tonometer according to claim 11, wherein said fixation means includes means for moving at least a part of said fixation means in the direction of an optical axis of the eye corresponding to the refractive power of the eye.

13. A non-contact tonometer according to claim 10, further comprising a fixation light source to be watched by the eye and a control means for changing a light emitting state of said fixation light source when the output of said light receiving element reaches a predetermined value.

14. An eye pressure meter according to claim 13, wherein said control means changes the output of said fixation light source between a flickering state and a turned-on state.

15. An eye pressure meter, comprising:
fluid pressurizing chamber means for providing pressurized fluid;
nozzle means for supplying the pressurized fluid to deform a cornea of an eye to be examined, said nozzle means being operably associated with said fluid pressurizing chamber means and adapted to be positioned opposite the eye along a pressurization axis;
projection means for projecting a pulse signal to the cornea;
receiving means for receiving the signal reflected by the cornea during the deformation of the cornea;
deformation speed detecting means for detecting the moving speed of the corneal surface being deformed in the direction of the pressurization axis on the basis of a frequency deviation between the pulse signal projected to the cornea and the signal reflected by the cornea; and
calculation means for calculating the eye pressure in accordance with the time integration of an output from said deformation speed detecting means.

16. A non-contact tonometer comprising:
a pressurizing system, a deformation detection system, and a calculation system, wherein:
said pressurizing system includes:
fluid pressurizing chamber means for providing pressurized fluid; and
nozzle means for applying the pressurized fluid to deform a cornea of an eye to be examined, said nozzle means being coupled to said fluid pressurizing chamber means and adapted to be positioned opposite the eye along a pressurization axis;
said deformation detection system includes:
light projection means for projecting a pulsed light beam to the cornea;
light receiving means for receiving a light beam reflected by the cornea during the deformation of the cornea; and
deformation speed detecting means for detecting the moving speed of the cornea being deformed in the direction of the pressurization axis on the basis of a frequency deviation between the pulsed light beam projected to the cornea and the pulsed light beam reflected by the cornea;
said calculation system includes:
calculation means for calculating the eye pressure in accordance with an extremum value of an output from said deformation speed detecting means.

17. A non-contact tonometer comprising:
a pressurizing system, a deformation detection system, and a calculation system, wherein:
said pressurizing system includes:
fluid pressurizing chamber means for providing pressurized fluid; and
nozzle means for applying the pressurized fluid to deform a cornea of an eye to be examined, said nozzle means being coupled to said fluid pressurizing means and adapted to be positioned opposite the eye along a pressurization axis;
said deformation detection system includes:
light projection means for projecting a light beam with a predetermined wavelength to the cornea;
light receiving means for receiving a light beam reflected by the cornea during the deformation of the cornea; and
deformation speed detecting means for detecting the moving speed of the cornea being deformed in the direction of the pressurization axis on the basis of wavelength deviation between the light beam projected to the cornea and the light beam reflected by the cornea;
said calculation system includes:
calculation means for calculating the eye pressure on the basis of the time integration of an output from said deformation speed detecting means.

18. A non-contact tonometer comprising:
a pressurizing system, a deformation detection system, and a calculation system, wherein:
said pressurizing system includes:
fluid pressurizing chamber means for providing pressurized fluid; and
nozzle means for applying the pressurized fluid to deform a cornea of an eye to be examined, said nozzle means being coupled to said fluid pressurizing chamber means and adapted to be positioned opposite the eye along a pressurization axis;
said deformation detection system includes:
light projection means for projecting a light beam with a predetermined wavelength to the cornea;
light receiving means for receiving a light beam reflected by the cornea during the deformation of the cornea; and
deformation speed detecting means for detecting the moving speed of the cornea being deformed in the direction of the pressurization axis on the basis of a wavelength deviation between the light beam projected to the cornea and the light beam reflected by the cornea;
said calculation system includes:
calculation means for calculating the eye pressure in accordance with an extremum value of an output from said deformation speed detecting means.

19. A non-contact tonometer comprising:
a pressurizing system, a deformation detection system, and a calculation system, wherein:
said pressurizing system includes:
pressurizing energy means for deforming a cornea of an eye to be examined, said pressurizing energy means being adapted to be positioned opposite the eye along a pressurization axis;
said deformation detection system includes:
light projection means for projecting a pulsed light beam to the cornea;
light receiving means for receiving a light beam reflected by the cornea during the deformation of the cornea; and
deformation speed detecting means for detecting the moving speed of the cornea being deformed in the direction of the pressurization axis on the basis of a frequency deviation between the pulsed light beam projected to the cornea and the light beam reflected by the cornea;
said calculation system includes:
calculation means for calculating the eye pressure on the basis of the time integration of an output from said deformation speed detecting means.

20. A non-contact tonometer comprising:
a pressurizing system, a deformation detection system, and a calculation system, wherein:
said pressurizing system includes:
pressurizing energy means for deforming a cornea of an eye to be examined, said pressurizing energy means being adapted to be positioned opposite the eye along a pressurization axis;
said deformation detection system includes:
light projection means for projecting a pulsed light beam to the cornea;
light receiving means for receiving a light beam reflected by the cornea during the deformation of the cornea; and
deformation speed detecting means for detecting the moving speed of the cornea being deformed in the direction of the pressurization axis on the basis of a frequency deviation between pulsed light beam projected to the cornea and the light beam reflected by the cornea;
said calculation system includes:
calculation means for calculating the eye pressure in accordance with an extremum value of an output from said deformation speed detecting means.

21. A non-contact tonometer comprising:
a pressurizing system, a deformation detection system, and a calculation system, wherein:
said pressurizing system includes:
pressurizing energy means for deforming a cornea of an eye to be examined, said pressurizing energy means being adapted to be positioned opposite the eye along a pressurization axis;
said deformation detection system includes:
light projection means for projecting a light beam with a predetermined wavelength to the cornea;
light receiving means for receiving a light beam reflected by the cornea during the deformation of the cornea; and
deformation speed detecting means for detecting the moving speed of the cornea being deformed in the direction of the pressurization axis on the basis of a wavelength deviation between the pulsed light beam projected to the cornea and the light beam reflected by the cornea;
said calculation system includes:
calculation means for calculating the eye pressure on the basis of the time integration of an output from said deformation speed detecting means.

22. A non-contact tonometer comprising:
a pressurizing system, a deformation detection system, and a calculation system, wherein:
said pressurizing system includes:
pressurizing energy means for deforming a cornea of an eye to be examined, said pressurization energy means being adapted to be positioned opposite the eye along a pressurization axis;
said deformation detection system includes:
light projection means for projecting a light beam with a predetermined wavelength to the cornea;
light receiving means for receiving a light beam reflected by the cornea during the deformation of the cornea; and
deformation speed detecting means for detecting the moving speed of the cornea being deformed in the direction of the pressurization axis on the basis of a wavelength deviation between the pulsed light beam projected to the cornea and the light beam reflected by the cornea;
said calculation system includes:
calculation means for calculating the eye pressure in accordance with an extremum value of an output from said deformation speed detecting means.

23. A non-contact tonometer comprising:
a pressurizing system, a deformation detection system, and a calculation system, wherein:
said pressurizing system includes:
fluid pressurizing chamber means for providing pressurized fluid; and
nozzle means for applying the pressurized fluid to deform a cornea of an eye to be examined, said nozzle means being coupled to said fluid pressurizing chamber means and adapted to be positioned opposite the eye along a pressurization axis;
said deformation detection system includes:
light projection means for receiving a light beam reflected by the cornea during the deformation of the cornea;
light receiving means for receiving a light beam reflected by the cornea during the deformation of the cornea; and
deformation speed detecting means for detecting the moving speed of the cornea being deformed in the direction of the pressurization axis on the basis of a frequency deviation between the pulsed light beam projected to the cornea and the light beam reflected by the cornea;
said calculation system includes:
calculation means for calculating the eye pressure on the basis of an output from said deformation speed detecting means.

24. A non-contact tonometer comprising:
a pressurizing system, a deformation detection system, and a calculation system, wherein:
pressurizing energy means for deforming a cornea of an eye to be examined, said pressurizing energy means being adapted to be positioned opposite the eye along a pressurization axis;
said deformation detection system includes:
light projection means for projecting a pulsed light beam to the cornea;
light receiving means for receiving a light beam reflected by the cornea during the deformation of the cornea; and
deformation speed detecting means for detecting the moving speed of the cornea being deformed in the direction of the pressurization axis on the basis of a frequency deviation between the pulsed light beam projected to the cornea and the light beam reflected by the cornea;
said calculation system includes:
calculation means for calculating the eye pressure on the basis of an output from said deformation speed detecting means.

25. A non-contact tonometer, comprising:

fluid pressurizing chamber means for providing pressurized fluid;

nozzle means for supplying the pressurized fluid to deform a cornea of an eye to be examined, said nozzle means being operably associated with said fluid pressurizing chamber means and adapted to be positioned opposite the eye along a pressurization axis;

projection means for projecting a pulse signal to the cornea;

receiving means for receiving the signal reflected by the cornea during the deformation of the cornea;

detecting means for detecting a frequency deviation between the pulse signal projected to the cornea and the signal reflected by the cornea; and calculation means for calculating the eye pressure on the basis of an output from said detecting means.

26. A non-contact tonometer according to claim 25, wherein said calculation means calculates the time integration of the output from said detecting means.

27. A non-contact tonometer according to claim 25, wherein said calculation means calculates an extended value of the output from said detecting means.

28. A non-contact tonometer, comprising:

a pressurizing system, a deformation detection system and a calculation system, wherein said pressurizing system includes pressurizing energy means for deforming a cornea of an eye to be examined, said pressurizing energy means being adapted to be positioned opposite the eye along a pressurization axis;

wherein said deformation detection system includes:
projection means for projecting a pulse signal to the cornea;

receiving means for receiving the signal reflected by the cornea during the deformation of the cornea;

detecting means for detecting a frequency deviation between the pulse signal projected to the cornea and the signal reflected by the cornea; and wherein said calculation system includes calculation means for calculating the eye pressure on the basis of an output from said detecting means.

29. A non-contact tonometer according to claim 28, wherein said calculation means calculates the time integration of the output from said detecting means.

30. A non-contact tonometer according to claim 28, wherein said calculation means calculates an extended value of the output from said detecting means.

* * * * *

UNITED STATES PATENT AND TRADEMARK OFFICE
CERTIFICATE OF CORRECTION

PATENT NO. : 5,076,274
DATED : December 31, 1991
INVENTOR(S) : KAZUHIRO MATSUMOTO It is certified that error appears in the above-identified patent and that said Letters Patent is hereby corrected as shown below:

COVER PAGE:

At [56], "182621  6/1986 European Pat. Off." should read -- 183621  6/1986 European Pat. Off. --.

COLUMN 2

Line 52, "before" should read -- before being --.

COLUMN 3

Line 44, "image 2" should read -- image 22'' --.

COLUMN 4

Line 11, "$\int_{I\infty} Vdt$" should read -- $\int^T_8 Vdt$ --.
Line 40, delete "to" (first occurrence).

UNITED STATES PATENT AND TRADEMARK OFFICE
CERTIFICATE OF CORRECTION

PATENT NO. : 5,076,274
DATED : December 31, 1991
INVENTOR(S) : KAZUHIRO MATSUMOTO It is certified that error appears in the above-identified patent and that said Letters Patent is hereby corrected as shown below:

COLUMN 6

Line 10, "pulsed" should read -- the pulsed --.

COLUMN 7

Line 7, "An eye pressure meter" should read -- A non-contact tonometer --.

Signed and Sealed this

Twenty-fifth Day of May, 1993

Attest:

MICHAEL K. KIRK

Attesting Officer

Acting Commissioner of Patents and Trademarks